United States Patent [19]

Elango et al.

[11] Patent Number: 5,744,648
[45] Date of Patent: Apr. 28, 1998

[54] PROCESS FOR THE MANUFACTURE OF 1,3-CYCLOHEXANEDIONE

[75] Inventors: Varadaraj Elango, Norwood, Mass.; Rajagopal Sakamuri, Warwick, R.I.

[73] Assignee: Hoechst Celanese Corporation, Somerville, N.J.

[21] Appl. No.: 690,792

[22] Filed: Aug. 1, 1996

[51] Int. Cl.[6] .................................................. C07C 45/29
[52] U.S. Cl. .................................................. 568/362
[58] Field of Search .................................... 568/362

[56] References Cited

U.S. PATENT DOCUMENTS

| | | | |
|---|---|---|---|
| 2,829,166 | 4/1958 | Joris et al. | 260/586 |
| 3,067,810 | 11/1962 | Mozic | 158/50.1 |
| 3,922,307 | 11/1975 | Muller | 260/586 C |
| 3,932,510 | 1/1976 | Muller | 260/586 R |
| 4,028,417 | 6/1977 | Muller et al. | 260/586 C |

FOREIGN PATENT DOCUMENTS

| | | |
|---|---|---|
| 219282 | 4/1987 | European Pat. Off. . |
| 331422 | 9/1989 | European Pat. Off. . |
| 2749437 | 5/1978 | Germany . |

OTHER PUBLICATIONS

Thompson, R.B. Organic Synthesis, Collective vol. 3:278 (1955).

Grob et al. Helvetica Chimica Acta 48: (4) 799 (1965).

Meek et al. J. Chem. Soc. 811(1953).

Kuhn et al. Ann 611: 57 (1958).

Mekler et al. Organic Synthesis Collective vol. 41:56 (1961).

Tamelen et al. J. Am. Chem. Soc. 78: 4405 (1956).

Esch et al. J. Am. Pharm. Assoc. Science Ed. 49: 786 (1960).

Smith et al. J. Am. Chem. Soc. 83: 2739 (1961).

Mokotoff et al. J. Org. Chem. 39:409 (1974).

Johnstone et al. Chem. Rev. 85: 129–170 (1985).

Rajagopal et al. J. Org. Chem. 60: 1347–1355 (1995).

Basava et al. (Ed.) *Peptides –Design, Synthesis, and Biological Activity*, Birkhauser, Boston (1994) pp. 11–26.

Hodges et al (Ed.) *Peptides –Chemistry, Structure and Biology*, Escom, Liedon (1994) pp. 190–192.

Burli et al. Specialty Chem. 13(6): 346–348 (1993).

*Primary Examiner*—James H. Reamer
*Attorney, Agent, or Firm*—Scott E. Hanf

[57] ABSTRACT

A new process for the manufacture of 1,3-cyclohexanedione is disclosed wherein a selected resorcinol is reduced with a hydrogen donor in the presence of a metal catalyst to produce a product which is then neutralized with an acid.

17 Claims, No Drawings

PROCESS FOR THE MANUFACTURE OF 1, 3-CYCLOHEXANEDIONE

BACKGROUND OF THE INVENTION

The product 1,3-cyclohexanedione (CHD) and substituted derivatives thereof are useful for making a variety of pharmaceutical and agricultural chemical products. Traditionally the manufacture of CHD and its derivatives has been accomplished in a variety of ways. For example, one method is the alkaline cyclization of ethyl or methyl 5-oxohexanoate as described in German Patent 2,749,437 assigned to Stamicarbon; and U.S. Pat. Nos. 3,922,307; 3,932,510 and 4,028,417 assigned to Hoechst A G. Other methods teach the hydrogenation of resorcinol and its derivatives using Raney nickel under various conditions. These methods include those described in: Thompson, R. B., *Organic Synthesis*, Coll. Vol. 3:278 (1955); European Patent Application 331,422 assigned to Mitsui Petrochemicals; Grob et al, *Helv. Chem. Acta*, 48(4):799 (1965); European Patent Application 219,282 assigned to Sumitomo Chemical Co. (also discusses the use of other catalysts such as ruthenium and rhodium on supports); Meek et al, *J. Chem. Soc.*, 811 (1953); Kuhn et al, *Ann*, 611:57 (1958); U.S. Pat. No. 2,829,166; U.S. Pat. No. 3,067,810; Mekler et al, *Organic Synthesis*, Coll. Vol. 41:56 (1961); and Tamalen et al, *J. Am. Chem. Soc.*, 78:4405 (1956). All of the previously described references describe the use of very high pressures and alkaline conditions to effect the reduction of resorcinol and its derivatives.

Yet another method for making CHD is the hydrogenation of resorcinol with hydrogen gas under pressure and alkaline conditions using noble metal catalysts. See Esch et al, *J. Am. Pharm. Assoc., Science Ed.*, 49:786 (1960) which teaches the use of Rh/Al$_2$O$_3$ and Pd/C in alkali; Smith et al, *J. Am. Chem. Soc.*, 83:2739 (1961) which teaches the use of 5% Rh/Al$_2$O$_3$ with alkali; and Mokotoff et al, *J. Org. Chem.*, 39:409 (1974) which teaches the use of 5% Rh/Al$_2$O$_3$ in alkali and pressure of 55 pounds per square inch (gauge) to hydrogenate 3,5-dihydroxyphenylacetic acid.

None of these methods has proven satisfactory, however, and each method suffers from one or more undesirable results. These undesirable results include: production of unwanted side products; obtaining CHD only in poor yields; the need for further significant purification steps to isolate good quality CHD; and the need to use strong base and high pressure reaction conditions. Thus, there remains a need for an alternate process for the manufacture of 1,3-cyclohexanedione and related compounds which process overcomes these problems.

In general, catalytic transfer hydrogenation/ hydrogenolysis is useful in organic chemistry. See, generally, Johnstone et al, *Chem. Rev.*, 85:129–170 (1985); Rajagopal et al, *J. Org. Chem.*, 60:1347–1355 (1995); Rajagopal et al, "Catalytic Transfer Hydrogenation and Hydrogenolysis by Formic Acid and Its Salts", *PEPTIDES—Design, Synthesis, and Biological Activity*, (Birkhäuser, Boston 1994) Basava et al (editors) pages 11–26; Hodges et al (editors) *PEPTIDES—Chemistry, Structure and Biology*, ESCOM, Leiden 1994), Paper by Rajagopal et al, pages 190–192, "Mechanistic studies on the hydrodechlorination reaction using sodium formate-catalytic transfer hydrogenation"; and Burli et al, "Hydrogen Transfer Reduction of Nitro Aromatic Compounds", *Specialty Chemicals*, 13(6): 346–348 (1993). It is believed, however, that such a technique has never been applied to the problem of making 1,3-cyclohexanedione from resorcinol.

In comparison with the catalytic reductions using molecular hydrogen, the transfer hydrogenations have many advantages: molecular hydrogen presents considerable hazards so avoidance of this is desirable, particularly when used on large scale. It is also more convenient to use conventional reactor vessels in place of pressure equipment and it is advantageous to obtain excellent yields and selectivities.

In approaching a solution to this problem it should be noted that 1,3-cyclohexanedione itself is unstable. It usually deteriorates on exposure to air, can be stored for only a short time, and has an increased tendency to give self-condensation products at high temperatures in the presence of catalysts. It is preferred that storage of 1,3-cyclohexanedione be under an inert atmosphere. A technique has now been found which produces 1,3-cyclohexanedione in excellent yield and purity without the need for harsh reaction conditions by using catalytic transfer hydrogenation.

SUMMARY OF THE INVENTION

It has been found that compounds of Formula I:

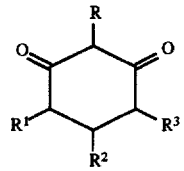

Formula I wherein each of R, R$^1$, R$^2$ and R$^3$ are independently selected from the group consisting of hydrogen; C$_1$–C$_6$ alkyl (preferably methyl, ethyl, propyl); C$_3$–C$_6$ cyclic alkyl; C$_1$–C$_6$ alkoxy (preferably methoxy and ethoxy); fluoro; trifluoromethyl; –(CH$_2$)$_n$–COOR$^5$ (where "n" is 0 to 6 and R$^5$ is H or C$_1$–C$_6$ alkyl); and phenyl, optionally substituted by a substituent which is inert to the present reduction process (for example, selected from the groups defined above for R, R$^1$, R$^2$ and $^3$R); may be made by a transfer hydrogenation process in which resorcinol (or a substituted resorcinol when any of R, R$^1$,R$^2$ and R$^3$ are other than hydrogen as described above) is reduced with a hydrogen donor in the presence of a metal catalyst selected from the group consisting of platinum, palladium, rhodium and ruthenium and a solvent to form a salt of the 1,3-diketone which is then converted to the compound of Formula I by neutralization with an acid.

DETAILED DESCRIPTION OF THE INVENTION AND DESCRIPTION OF THE PREFERRED EMBODIMENT

According to the method of this invention as represented in Reaction Scheme I:

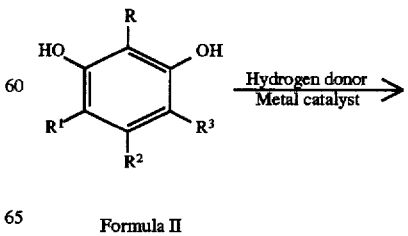

Formula II

-continued
Scheme I

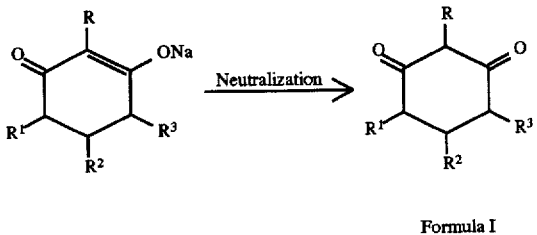

Formula I a compound of Formula II wherein each of R, $R^1$, $R^2$ and $R^3$ is independently selected from the groups defined above may be used to obtain a compound of Formula I.

The hydrogen donor which may be used for the reaction of the present invention may be selected from the group consisting of $C_3$–$C_6$ secondary alcohols (such as isopropanol), cyclohexene, hydrazine, phosphinic acid, sodium hypophosphite, potassium hypophosphite, indoline, formic acid, and formate salts derived from ammonia, triethylamine, alkali or alkaline earth elements (particularly sodium and potassium). Among the hydrogen donors, formic acid and its salts are preferred with sodium formate and ammonium formate being more preferred. The use of formic acid or its salts gives environmentally benign $CO_2$ as a by-product and the hydrogen donation is irreversible. The reactants (the compound of Formula II and the hydrogen donor) can be mixed in equimolar quantities or the hydrogen donor can be used in excess. Preferably, a slight excess, typically a 5 to 25 mole % excess, most preferably a 5 to 15 mole % excess of the hydrogen donor is used to drive the reaction to completion.

The catalyst may be any conventional hydrogenation-dehydrogenation catalyst with or without a supporting medium. Examples of such catalysts are metal catalysts selected from the group consisting of ruthenium, rhodium, platinum and palladium. Catalyst supports may include carbon, alma, silica, silica-alumina, clay, zeolites etc. Preferably, a supported metal catalyst, most preferably palladium on carbon, is utilized in catalytic amounts in the present invention. The concentration of metal on the catalyst support can vary over a wide range, but typically 3–20% and preferably 3–5% of metal catalyst on the catalyst support is used. The metal catalyst on a support is used in an amount of from about 0.001 to 20 weight %, preferably from about 0.1 to 10 weight %, based on the amount of the compound of Formula II used.

Suitable solvents for the reaction are water, $C_1$–$C_6$ alcohols, and any solvent inert to the reaction conditions. Preferably, water or alcohol or mixtures thereof are employed. Suitable alcohol solvents include methanol, ethanol, isopropanol, and the like. Alcohol/water mixtures include those with an alcohol:water ratio in the range of 1:10 to 10:1. The solvent is used in a ratio of about 1.0–10.0 parts, preferably about 1.0–4.0 parts per one part of compound of Formula II.

The reaction is carried out under acidic to alkaline conditions such as at a pH of 4–14, preferably 5–11 and more preferably at a pH of 5–9. The reaction may optionally include the addition of a base selected from the group consisting of sodium hydroxide, potassium hydroxide, sodium carbonate, potassium carbonate, sodium bicarbonate and potassium bicarbonate to maintain the pH. The effective reaction temperature is from about 10° C. to about 100° C., preferably from about 20° C. to about 70° C.; however, higher temperatures may be used depending upon the boiling point of the solvent. The reaction is typically allowed to proceed until most of the compound of the Formula II is consumed as indicated by HPLC or gas chromatography.

When most of the starting material of Formula II has been consumed (about 98 percent), the reaction mixture is separated from the catalyst by conventional means such as filtration. The reaction mixture is then neutralized with a mineral acid such as HCl or $H_2SO_4$, preferably HCl, until the pH is lowered to at least 3 to form the compound of Formula I. Any conventional separation means may be utilized to isolate the compound of Formula II such as centrifugation, chromatographic separation or crystallization followed by filtration. Preferably crystallization followed by filtration is used.

In a particularly preferred embodiment shown in Reaction Scheme II:

Scheme II

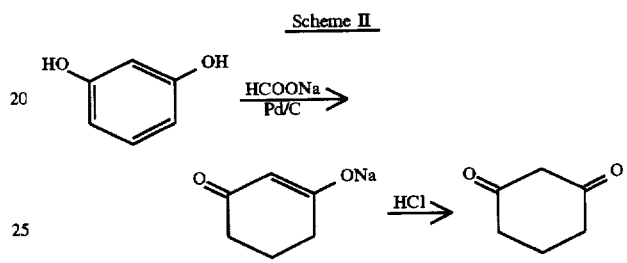

1,3-cyclohexanedione is made by combining resorcinol with sodium formate in water using 5% palladium on carbon in water at a pH of 5–11. Sodium formate is added in an amount of 1.0–1.25 mole equivalents with 0.5–10 weight % (and more particularly 1–5%) of a Pd/C catalyst at a reaction temperature of 40°–70° C. for 1–15 hours. After the completion of the reaction, the catalyst is separated by filtration. Next, a sufficient amount of concentrated HCl is added to lower the pH of the mixture to about 3, and the reaction is cooled and stirred for an additional 0.5–4.0 hours. Optionally, sodium chloride may be added to facilitate recovery of 1,3-cyclohexanedione. The product is then recovered by filtration in a yield of greater than 89%.

Note that in the Reaction Schemes I and II, the final product of Formula I is characterized by a highly reactive methylene group between two activating carbonyls. Consequently, the 1,3-cyclodiketone exists as an equilibrium mixture with the enolic form. The equilibrium distribution varies with the structure and solvent.

In a particular example, a compound of Formula I is made wherein each of R, $R^1$, $R^2$ and $R^3$ are independently selected from the group consisting of hydrogen; $C_1$–$C_6$ alkyl; $C_3$–$C_6$ cyclic alkyl, $C_1$–$C_6$ alkoxy; fluoro; trifluoromethyl; –($CH_2$)$_n$–$COOR^5$ (where n is 0 to 6 and $R^5$ is H or $C_1$–$C_6$ alkyl); and phenyl, optionally substituted by a substituent which is selected from the groups defined for R, $R^1$, $R^2$ and $R^3$, wherein said method comprises a transfer hydrogenation process in which resorcinol or substituted resorcinol of Formula II:

Formula II

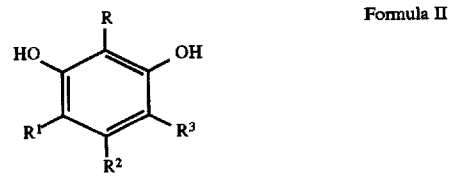

is reduced with a hydrogen donor in the presence of a noble metal catalyst and a solvent to form a salt of a corresponding 1,3-diketone which diketone is then converted to the compound of Formula I by neutralization with an acid and wherein, when at least 98% of the compound of Formula II has been consumed, the reaction mixture is (a) filtered to remove the catalyst; and (b) acidified to a pH of at least 3.

EXAMPLES

The following Examples are illustrative of the invention but should not be construed as limitations thereon. Unless otherwise indicated, all chemical symbols, abbreviations and nomenclature have their usual and customary meanings. Percents are in weight percents, temperatures are measured in degrees Centigrade.

Example 1

A 500 ml four-neck flask fitted with a mechanical stirrer, a thermocouple, a gas inlet and a reflex condenser was charged with 125 ml of water, 55.0 g of resorcinol and 40.8 g of sodium formate. The reaction mixture was heated to 40° C. while stirring and purging the reaction medium with nitrogen gas for 20 minutes. At this temperature, 2.0 g of 50% wet 5% Pd/C catalyst were added and held for 3 hours. The reaction mixture was then heated to 50° C. for another 3.0 hours. The reaction was analyzed by HPLC which indicated greater than 98% conversion and greater than 96% selectivity. At the end of the reaction, the mixture was filtered while still hot to remove the catalyst. The filtrate was cooled to 0°–5° C. by external means while adjusting the pH to 3.0 with concentrated hydrochloric acid. Sodium chloride (40 g) was then added over 20 minutes. The precipitated solids were isolated by filtration and dried to obtain 52 g of 1,3-cyclohexanedione (yield, 91%).

Example 2

A 500 ml flask was charged with 125 ml of water, 20 g of 50% sodium hydroxide, 55.0 g of resorcinol and 40.8 g of sodium formate. The reaction mixture was heated to 40° C. while stirring and the reaction medium was purged with nitrogen gas for 20 minutes. Two grams of 50% wet 5% Pd/C catalyst were added and held for 3 hours. The reaction mixture was then heated to 50° C. for another 3.0 hours. The reaction was analyzed by HPLC which indicated greater than 98% conversion and greater than 96% selectivity. At the end of the reaction, the mixture was filtered while hot to remove the catalyst. The filtrate was cooled to 0°–5° C. by external means while adjusting the pH adjusted to 3.0 with concentrated hydrochloric acid. Sodium chloride (30 g) was then added over 20 minutes. The precipitated solids were isolated by filtration (yield, 90%).

Example 3

A mixture of 125 ml of water, 55.0 g of resorcinol, 40.8 g of sodium formate and 25 g of 37.5% aqueous hydrochloric acid was heated to 30° C. while stirring and purging the reaction medium with nitrogen gas. At this temperature, 2.0 g of 50% wet 5% Pd/C catalyst were added and held for 4 hours. The reaction was analyzed by HPLC which indicated greater than 98% conversion and greater than 96% selectivity. The reaction mixture was clarified to remove the catalyst. The filtrate was cooled to 0°–5° C. by external means while adjusting the pH adjusted to 3.0 with concentrated hydrochloric acid. Sodium chloride (35 g) was then added. The precipitated solids were isolated by filtration (yield, 89%).

Example 4

The reaction was carried out in the same manner as in Example 1, except that 50% wet 5% Pd/C powder was replaced with 50% wet 5% Pd/C egg-shell type catalyst. The reaction was analyzed by HPLC which indicated greater than 98% conversion and greater than 96% selectivity. The isolated yield of 1,3-cyclohexanedione was 90%.

Example 5

The reaction was carried out in the same manner as in Example 1, except that 5% Pd/SiO$_2$ was used as the catalyst. The reaction was analyzed by HPLC which indicated greater than 98% conversion and greater than 96% selectivity. The isolated yield of 1,3-cyclohexanedione was 91%.

Example 6

A 500 ml flask fitted with a mechanical stirrer, a thermocouple, a gas inlet and a reflex condenser was charged with 125 ml of water, 55.0 g of resorcinol and 37.8 g of ammonium formate. The reaction mixture was heated to 30° C. while stirring and purging the reaction medium with nitrogen for 20 minutes. At this temperature, 2.0 g of 50% wet 5% Pd/C catalyst were added and held for 3 hours. The reaction mixture was then heated to 40° C. for 1.0 hour. The reaction was analyzed by HPLC which indicated greater than 98% conversion and greater than 96% selectivity. After the reaction was completed, the product was isolated in the same manner as in Example 1 to provide 90% yield.

Example 7

Ethanol was used as a solvent in place of water and the reaction was carried out in the same manner as in Example 6. After completion of the reaction, the catalyst was filtered off and the filtrate was analyzed by liquid chromatography. Resorcinol conversion was 99% and 1,3-cyclohexanedione selectivity was greater than 96%.

Example 8

A part of water (50%) was replaced with ethanol as a solvent and the reaction was carried out in the same manner as in Example 6. After completion of the reaction, the catalyst was filtered off and the filtrate was analyzed by liquid chromatography. Resorcinol conversion was 98% and 1,3-cyclohexanedione selectivity was greater than 96%.

We claim:

1. A method for making a compound of Formula I:

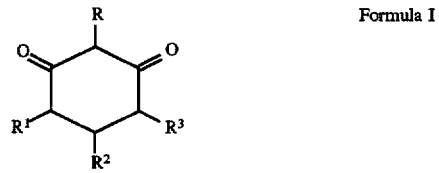

Formula I wherein each of R, R$^1$, R$^2$ and R$^3$ are independently selected from the group consisting of hydrogen; C$_1$–C$_6$ alkyl; C$_3$–C$_6$ cyclic alkyl; C$_1$–C$_6$ alkoxy; fluoro; trifluoromethyl; –(CH$_2$)$_n$–COOR$^5$ (where n is 0 to 6 and R$^5$ is H or C$_1$–C$_6$ alkyl); and phenyl, optionally substituted by a substituent selected from the groups defined above for R, R$^1$, R$^2$ and R$_3$; wherein said method comprises a transfer hydrogenation process in which resorcinol or substituted resorcinol of Formula II:

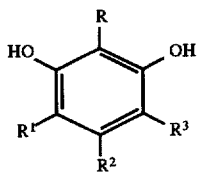

Formula II is reduced with a hydrogen donor in the presence of (a) a metal catalyst selected from the group consisting of platinum, palladium rhodium and ruthenium, and (b) a solvent to form a salt of a corresponding 1,3-diketone which diketone is then converted to the compound of Formula I by neutralization with an acid.

2. The method of claim 1 wherein the $C_1$–$C_6$ alkyl is methyl, ethyl or propyl.

3. The method of claim 1 wherein the $C_1$–$C_6$ alkoxy is methoxy or ethoxy.

4. The method of claim 1 wherein the hydrogen donor is selected from the group consisting of $C_3$–$C_6$ secondary alcohols; cyclohexene; hydrazine; phosphinic acid; sodium hypophosphite, potassium hypophosphite; indoline; formic acid; and formate salts derived from ammonia, triethylamine, alkali or alkaline earth elements.

5. The method of claim 4 wherein the secondary alcohol is isopropanol.

6. The method of claim 4 wherein the hypophosphite is sodium hypophosphite.

7. The method of claim 4 wherein the hydrogen donor is selected from formic acid and salts thereof.

8. The method of claim 7 wherein the hydrogen donor is sodium formate or ammonium formate.

9. The method of claim 1 wherein the catalyst is a supported or unsupported catalyst selected from a group of metal catalysts consisting of platinum, palladium, rhodium and ruthenium.

10. The method of claim 9 wherein the catalyst is supported and the support is selected from the group consisting of carbon, alumina, silica, silica-alumina, clay, and zeolites.

11. The method of claim 10 wherein the metal catalyst on a support is used in an amount of from about 0.001 to 20 weight %.

12. The method of claim 10 wherein the catalyst is palladium on a carbon support.

13. The method of claim 1 wherein the solvent is selected from the group consisting of water, $C_1$–$C_6$ alcohols, and mixtures of water and a $C_1$–$C_6$ alcohol.

14. The method of claim 1 wherein the reaction takes place at a pH in the range of 4–14.

15. The method of claim 1 wherein the reaction takes place at a pH in the range of 5–11.

16. The method of claim 1 wherein the reaction takes place at a pH in the range of 5–9.

17. A method for making a compound of Formula I:

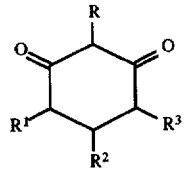

Formula I wherein each of R, $R^1$, $R^2$ and $R^3$ are independently selected from the group consisting of hydrogen; $C_1$–$C_6$ alkyl; $C_3$–$C_6$ cyclic alkyl, $C_1$–$C_6$ alkoxy; fluoro; trifluoromethyl; –$(CH_2)_n$–$COOR^5$ (where n is 0 to 6 and $R^5$ is H or $C_1$–$C_6$ alkyl); and phenyl, optionally substituted by a substituent which is selected from the groups defined for R, $R^1$, $R^2$ and $R^3$; wherein said method comprises a transfer hydrogenation process in which resorcinol or substituted resorcinol of Formula II:

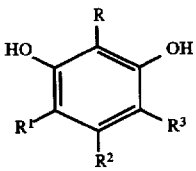

Formula II is reduced with a hydrogen donor in the presence of a noble metal catalyst and a solvent to form a salt of a corresponding 1,3-diketone which diketone is then converted to the compound of Formula I by neutralization with an acid and wherein, when at least 98% of the compound of Formula II has been consumed, the reaction mixture is (a) filtered to remove the catalyst; and Co) acidified to a pH of at least 3.

* * * * *